United States Patent
van Rens

(10) Patent No.: US 11,628,472 B2
(45) Date of Patent: Apr. 18, 2023

(54) CAPACITIVE MICRO-MACHINED ULTRASOUND TRANSDUCER (CMUT) DEVICES

(71) Applicant: KONINKLIJKE PHILIPS N.V., Eindhoven (NL)

(72) Inventor: Antonia Cornelia van Rens, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 360 days.

(21) Appl. No.: 16/862,030

(22) Filed: Apr. 29, 2020

(65) Prior Publication Data
US 2020/0346248 A1 Nov. 5, 2020

(30) Foreign Application Priority Data
Apr. 30, 2019 (EP) .................................... 19171719

(51) Int. Cl.
*B06B 1/02* (2006.01)
*A61B 8/00* (2006.01)
(Continued)

(52) U.S. Cl.
CPC .......... *B06B 1/0292* (2013.01); *A61B 8/4494* (2013.01); *B06B 1/0207* (2013.01);
(Continued)

(58) Field of Classification Search
CPC . B06B 1/0292; B06B 1/0207; B06B 2201/20; B06B 2201/51; A61B 8/4494;
(Continued)

(56) References Cited

U.S. PATENT DOCUMENTS 6,120,449 A 9/2000 Snyder et al.
6,328,696 B1 * 12/2001 Fraser .................. B06B 1/0292
600/459
(Continued)

FOREIGN PATENT DOCUMENTS

WO 2015086413 A1 6/2015
WO 2019030045 A1 2/2019

OTHER PUBLICATIONS

European Search Report for European Application No. 19171719.8, filed Apr. 30, 2019, 7 pages.

*Primary Examiner* — Jacques M Saint Surin

(57) ABSTRACT

An ultrasound system has a set of CMUT ultrasound transducer devices and a drive circuit for operating the ultrasound transducer devices, for delivering an AC drive signal and receiving a reflected signal. An intermediate circuit is between the drive circuit and the set of ultrasound devices in the form of an array of coupling circuits, each coupling circuit between the drive circuit and an associated at least one ultrasound transducer device. Each coupling circuit comprises a buffer element connected between a bias voltage and a device terminal and as series capacitor. The intermediate circuit serves as a connection link between the set of CMUT transducer elements and the driving/sensing electronics, and is formed as a passive integrated technology circuit. The buffer element prevents a low-impedance short between the CMUT cell bias node and the counter electrode in the case of a CMUT cell drum short circuit. In this way, failure of an individual cell will not cause a breakdown of the whole CMUT array nor a breakdown of the driving electronics.

21 Claims, 7 Drawing Sheets

(51) Int. Cl.
*G01S 7/52* (2006.01)
*G01S 15/89* (2006.01)

(52) U.S. Cl.
CPC ...... *G01S 7/52046* (2013.01); *G01S 7/52079* (2013.01); *G01S 15/8925* (2013.01); *G01S 15/8993* (2013.01); *B06B 2201/51* (2013.01)

(58) Field of Classification Search
CPC ............ G01S 7/52046; G01S 7/52079; G01S 15/8925; G01S 15/8993
USPC ........................................................ 600/459
See application file for complete search history.

(56) References Cited

U.S. PATENT DOCUMENTS

| | | | |
|---|---|---|---|
| 6,328,697 B1 * | 12/2001 | Fraser | B33Y 80/00 600/459 |
| 6,443,901 B1 * | 9/2002 | Fraser | B06B 1/0292 600/459 |
| 7,745,973 B2 * | 6/2010 | Bayram | B06B 1/0292 310/328 |
| 8,309,428 B2 * | 11/2012 | Lemmerhirt | A61B 8/00 438/455 |
| 8,658,453 B2 * | 2/2014 | Lemmerhirt | B06B 1/0292 257/415 |
| 2018/0015504 A1 | 1/2018 | Zhao et al. | |
| 2018/0071775 A1 | 3/2018 | Zhuang et al. | |
| 2018/0164418 A1 | 6/2018 | Zemp et al. | |
| 2018/0310916 A1 | 11/2018 | Loebl et al. | |

* cited by examiner

CAPACITIVE MICRO-MACHINED ULTRASOUND TRANSDUCER (CMUT) DEVICES

RELATED APPLICATION

This application claims priority to and the benefit of European Application Serial No. 19171719.8, filed Apr. 30, 2019. This application is incorporated by reference herein in its entirety.

FIELD OF THE INVENTION

This invention relates to ultrasonic transducer probes which use capacitive micromachined ultrasonic transducers (CMUTs), for example for medical diagnostic ultrasonic imaging.

BACKGROUND OF THE INVENTION

Ultrasonic transducers used for medical imaging have numerous characteristics that lead to the production of high quality diagnostic images.

Traditionally, piezoelectric materials have been used for ultrasonic transducers. Examples are lead zirconate titanate (PZT) and polyvinylidene difluoride (PVDF) materials, with PZT being particularly popular as the material of choice. Single crystal piezoelectric materials are used to achieve high piezoelectric and electro-mechanical coupling constants for high performance transducers.

Recent developments have led to the prospect that medical ultrasound transducers can be batch manufactured by semiconductor processes. Desirably these processes should be the same ones used to produce the application specific integrated circuits (ASICs) needed by an ultrasound probe such as a CMOS process, particularly for 3D ultrasound. These developments have produced micro machined ultrasonic transducers or MUTs. MUT transducers are tiny diaphragm-like devices with electrodes that convert the sound vibration of a received ultrasound signal into a modulated signal.

Two such transducer types are those which utilize a piezoelectric material on the membrane called piezoelectric micromachined ultrasonic transducers (PMUTs) and those which utilize a capacitive effect between a conductive membrane and another electrode called capacitive micromachined ultrasonic transducers (CMUTs).

CMUT transducers in particular are able to function over a broad bandwidth, enable high resolution and high sensitivity imaging, and produce a large pressure output so that a large depth of field of acoustic signals can be received at ultrasonic frequencies.

For transmission, the capacitive charge applied to the electrodes is modulated to vibrate/move the diaphragm of the device and thereby transmit an ultrasound wave. Since these diaphragms are manufactured by semiconductor processes the devices generally can have dimensions in the 10-500 micrometer range, with the diaphragm diameter for instance being selected to match the diaphragm diameter to the desired resonance frequency (range) of the diaphragm, with spacing between the individual diaphragms less than a few micrometers. Many such individual CMUT cells can be connected together and operated in unison as a single transducer element. For example, four to sixteen CMUT cells can be coupled together to function in unison as a single transducer element. A typical 2D transducer array can have 2000-10000 CMUT transducer elements or cells by way of example.

Since these cells are very small, each MUT cell only produces or responds to a small amount of acoustic energy. Two approaches are commonly used to increase the acoustic efficiency of MUT devices.

One is to bias the cells with a DC bias voltage which, in the case of CMUTs, brings the vibrating membrane into close proximity to the opposing electrode, increasing the sensitivity of the devices. This is called a collapsed mode of operation. In this way, the acoustic power (output pressure) produced by the CMUT cells is optimized. The cells are provided with a stimulus signal having a set frequency that causes the diaphragm or flexible membrane to resonate at the set frequency. The DC voltage at which the membrane goes into collapse is called the collapse voltage, $V_c$. The DC bias voltage is typically a common signal to all cells.

Another is to form an array of cells which are very close to each other, maximizing the density of the cells on their substrate and providing a large number of cells which are operated in unison as a single transducer element. The high density fabrication of the cells also improves their grating lobe characteristics and reduces clutter in the resultant ultrasonic images.

A transducer array or even an individual element can thus comprise hundreds or thousands of individual MUT cells which are biased by the DC bias voltage. While such an architecture has numerous performance advantages as described above, a problem arises in that the failure of a single MUT cell can render a vast number of cells inoperative. It is possible for a single cell to fail by collapse of the membrane with its high DC bias voltage onto the opposing electrode. This shorts out not only the failed cell, but also all of the hundreds or thousands of other cells with which it is commonly biased. While the failure of a single cell by itself may not appreciably affect the performance of the transducer probe, the shorting out of a large number of other cells can render the entire transducer probe inoperative.

One approach to prevent this problem is described in U.S. Pat. No. 7,293,462 (Lee et al.). The approach of Lee et al. is to form a fuse at the end of a row or column of interconnected MUT cells which will open when one cell in the row or column shorts out. This will remove the row or column of cells from operation in the transducer, allowing the other cells in the transducer to remain functioning.

There are several drawbacks to this approach, however. One is that each row or column of interconnected cells must be separately biased, increasing the complexity of providing bias voltages to all of the cells in the probe. Another is that a fuse occupies a relatively large area on the MUT substrate, decreasing the area on the substrate available for MUT cells and hence the sensitivity of the transducers. Yet another is that a plurality of cells are removed from operation in the probe, the failed cell as well as the others to which it is connected, which also degrades the performance of the ultrasound probe.

It would be desirable to be able to maintain operation of system even in the presence of a failed cell, by allowing the other fully functioning cells to remain in operation.

SUMMARY OF THE INVENTION

The invention is defined by the claims.

According to examples in accordance with an aspect of the invention, there is provided an ultrasound system, comprising:

a set of ultrasound transducer devices, each device comprising one or more capacitive micro-machined ultrasound transducer cells each having first and second terminals;

a drive circuit for operating the ultrasound transducer devices, for delivering an AC drive signal and receiving a reflected signal at a drive circuit port associated with at least one of the ultrasound transducer devices, wherein the drive circuit comprises an ASIC; and an intermediate circuit between the drive circuit and the set of ultrasound devices, wherein the intermediate circuit comprises an array of coupling circuits, each coupling circuit between a drive circuit port and the associated at least one ultrasound transducer device, and comprising a buffer element connected between a bias voltage terminal and the first terminal and a capacitor in series between the first terminal and the drive circuit port, wherein the intermediate circuit comprises a passive integration technology circuit.

This system uses an additional system component, the intermediate circuit, which serves as a connection link between the set of CMUT transducer elements and the driving/sensing electronics. The buffer element prevents a low-impedance short between the CMUT cell bias node (wherefrom a DC bias voltage is supplied to the CMUT cell) and the counter electrode in the case of a CMUT cell drum short circuit. In this way, failure of an individual cell will not cause a breakdown of the whole CMUT array nor a breakdown of the driving electronics. The bias voltage terminals are for example all connected together to a common bias voltage supply.

The capacitor in series with the first terminal means the intermediate circuit enables a reduction in cross talk between the CMUT cells. Such crosstalk is for example likely when a common capacitor is used for stabilization of the CMUT bias voltage. By providing a set of series capacitors, the single common capacitor is replaced by many, smaller, capacitors in a circuit array.

The implementation of the intermediate circuit as a passive integration technology circuit, i.e. using passive integrated devices technology, means the production of the intermediate circuit is optimized, in that passive integration technologies are optimized for the realization of hundreds of compact passive components with high performance.

The intermediate circuit also enables new ways of driving and sensing the CMUT array as discussed further below.

The buffer element for example comprises a resistor. Thus, it provides a real impedance to the bias voltage.

The resistor-capacitor pair defines a T-network, and the intermediate circuit thus comprises an array of such bias-T networks.

In one set of examples, the second terminals may all be connected together, and the drive circuit port comprises a single drive circuit terminal. This provides a simple connection scheme, with only one CMUT cell terminal needing connection to the drive circuit. The drive circuit may then comprise a transmitter and a receiver connected to the single drive circuit terminal.

In another set of examples, the drive circuit port comprises first and second drive circuit terminals. This enables separate connection to the first and second device terminals.

In one example with two drive circuit terminals, the drive circuit comprises a differential transmitter connected to the first and second drive circuit terminals and a differential receiver connected to the first and second drive circuit terminals. This provides a differential implementation. The decoupling of the bias voltage achieved with the intermediate circuit enables a simpler realization of a differential implementation. Differential driving for example has the advantage that the driving pulse can have an amplitude which is double the supply voltage.

In another example with two drive circuit terminals, the drive circuit comprises a transmitter connected to the first drive circuit terminal and a receiver connected to the second drive circuit terminal. This enables separated driving and receiving electronics. The decoupling of the bias voltage allows the transmitter and receiver to have the same ground reference. It also enables the need for a transmit-receive switch to be avoided.

In all examples above, the set of ultrasound transducer devices may be a 1D array of transducer devices and each drive circuit port (whether a single terminal or two terminals) connects to a single ultrasound transducer device.

However, another set of examples makes use of a 2D array of transducer devices. Thus, the set of ultrasound transducer devices is an array of rows and columns of transducer devices, The drive circuit may then be a first drive circuit and the intermediate circuit is a first intermediate circuit, wherein each port of the first drive circuit connects to the first terminals of a row of ultrasound transducer devices through the first intermediate circuit.

The device then further comprises:

a second drive circuit (330) for delivering an AC drive signal and receiving a reflected signal at a second drive circuit port associated with at least one of the ultrasound transducer devices, wherein the second drive circuit is an ASIC; and a second intermediate circuit (332) between the second drive circuit and the set of ultrasound devices, wherein the second intermediate circuit comprises an array of coupling circuits, each coupling circuit between a second drive circuit port and the associated at least one ultrasound transducer device, and comprising a buffer element connected between a bias voltage terminal and the second terminal and a capacitor in series between the second terminal and the second drive circuit port, wherein the second intermediate circuit comprises a passive integration technology circuit, Each port of the second drive circuit connects to the second terminals of a column of ultrasound transducer devices through the second intermediate circuit.

In this way, a bi-planar 1D array is formed. The rows and columns may be controlled in the same way, so that equal quality images are obtained in the two planes.

The, or each, drive circuit for example comprises an ASIC. The, or each, intermediate circuit is preferably located physically proximate the set of ultrasound transducer devices.

The, or each, CMUT cell of each device is preferably adapted to be operated in a collapsed mode. This is achieved by the bias voltage applied. The invention is particularly suitable for devices which comprise CMUT cells operated in collapsed mode, for which the DC bias controls the collapse.

The, or each, CMUT cell of each device for example comprises:

a substrate;

a first electrode connected to the substrate formed around a central axis;

a flexible membrane, wherein the flexible membrane is at least partially spatially separated from the first electrode; and a second electrode connected to the flexible membrane, wherein the second electrode is concentric with the first electrode.

This defines an electrode layout for a collapsible CMUT cell.

The drive electronics for example comprises a capacitance sensing circuit which is used to measure a variation in the cell's capacitance as the response of the cell to an incident ultrasound stimulus and thereby enable ultrasound imaging. The ultrasound system for example comprises an imaging system.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
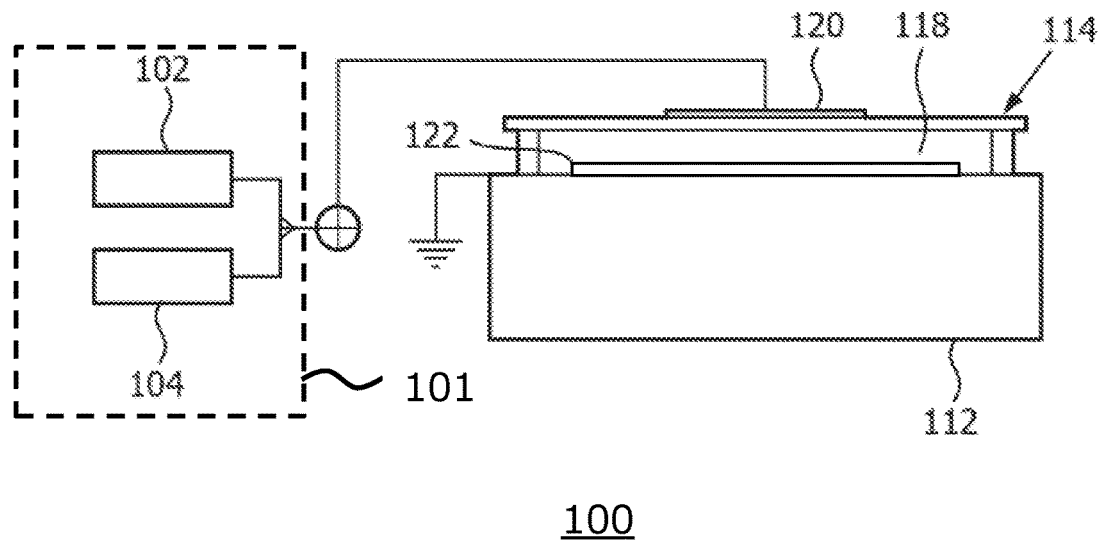
FIG. 1 schematically depicts a typical CMUT cell of an ultrasound system operable in a collapsed mode.

It should be understood that the Figures are merely schematic and are not drawn to scale. It should also be understood that the same reference numerals are used throughout the Figures to indicate the same or similar parts.

The invention provides an ultrasound system comprising a set of CMUT ultrasound transducer devices and a drive circuit for operating the ultrasound transducer devices, for delivering an AC drive signal and receiving a reflected signal. An intermediate circuit is between the drive circuit and the set of ultrasound devices in the form of an array of coupling circuits, each coupling circuit between the drive circuit and an associated at least one ultrasound transducer device. Each coupling circuit comprises a buffer element (preferably a resistor) connected between a bias voltage and a device terminal and a series capacitor, and is formed as a passive integrated technology circuit. The intermediate circuit serves as a connection link between the set of CMUT transducer elements and the driving/sensing electronics. The buffer element prevents a low-impedance short between the CMUT cell bias node and the counter electrode in the case of a CMUT cell drum short circuit. In this way, failure of an individual cell will not cause a breakdown of the whole CMUT array nor a breakdown of the driving electronics.

FIG. 1 shows a known design of CMUT cell 100 for use in an ultrasound system and a known drive arrangement 101. The CMUT cell 100 comprises a flexible membrane or diaphragm 114 suspended above a silicon substrate 112 with a gap or cavity 118 there between. A first electrode 122 is located on the floor of the cell on the upper surface of the substrate 112 in this example. A second electrode 120 is located on the diaphragm 114 and moves with the diaphragm. In the example shown, the two electrodes are circular.

A dielectric (not shown) is provided on the substrate 112 and underneath the top (second) electrode 120. These two dielectrics may be equal in composition and thickness, but may be also asymmetric (different materials and thicknesses).

The membrane layer 114 is fixed relative to the top face of the substrate layer 112 and configured and dimensioned so as to define a spherical or cylindrical cavity 118 between the membrane layer 114 and the substrate layer 112.

Other realizations of the electrode 120 design can be considered, such as electrode 120 may be embedded in the membrane 114 or it may be deposited on the membrane 114 as an additional layer. In this example, the first electrode 122 is circularly configured and embedded in the substrate layer 112 by way of non-limiting example. Other suitable arrangements are possible, such as other electrode shapes and other locations of the first electrode 122. The first electrode may be directly exposed to the gap 118 or separated from the gap 118 by an electrically insulating layer or film to prevent a short-circuit between the second electrode 120 and the first electrode 122.

In FIG. 1 the first electrode 122 is grounded by way of non-limiting example. Other arrangements, e.g. a grounded second electrode 120 or both second electrode 120 and first electrode 122 floating are of course equally feasible.

The cell 100 and its gap 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell. In FIG. 1, the diameter of the cylindrical cavity 118 is larger than the diameter of the circularly configured electrode plate 122. Electrode 120 may have the same outer diameter as the circularly configured electrode plate 122, although such conformance is not required and FIG. 1 shows a larger electrode plate 122.

The electrodes of the CMUT cell 100 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 100 to a received acoustic echo.

The spacing between the electrodes is controlled by applying a static voltage, e.g. a DC bias voltage, to the electrodes with a voltage supply 101. The voltage supply 101 may optionally comprise separate stages 102, 104 for providing the DC and AC or stimulus components respectively of the drive voltage of the CMUT cells 100, e.g. in transmission mode. The first stage 102 may be adapted to generate the static (DC) voltage component and the second stage 104 may be adapted to generate an alternating variable drive or stimulus voltage component having a set alternating frequency, which signal typically is the difference between the overall drive voltage and the aforementioned static component thereof.

The static or bias component of the applied drive voltage preferably meets or exceeds the threshold voltage for forcing the CMUT cell 100 into its collapsed state. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component.

Other suitable embodiments of the voltage source supply 101 should be apparent, such as for instance an embodiment in which the voltage source supply 101 contains three discrete stages including a first stage for generating the static DC component of the CMUT drive voltage, a second stage for generating the variable but DC component of the drive voltage and a third stage for generating the frequency modulation or stimulus component of the signal, e.g. a pulse circuit or the like. It is summarized that the voltage source supply 101 may be implemented in any suitable manner.

It is known that by applying a static voltage above a certain threshold, the CMUT cell 100 is forced into a collapsed state in which the membrane 114 collapses onto the substrate 112. This threshold value may depend on the exact design of the CMUT cell 100 and is defined as the DC bias voltage, known as the collapse voltage, at which the membrane 114 sticks to (contacts) the cell floor through the force due to the electric field between the electrodes. The amount (area) of contact between the membrane 114 and the substrate 112 is dependent on the applied bias voltage.

Increasing the contact area between the membrane 114 and the substrate 112 increases the resonant frequency of the membrane 114, as will be explained in more detail with the aid of FIG. 2a and FIG. 3a.

The frequency response of a collapsed mode CMUT cell 100 may be varied by adjusting the DC bias voltage applied to the CMUT electrodes after collapse. As a result, the resonant frequency of the CMUT cell increases as a higher DC bias voltage is applied to the electrodes.

Figure 2A:
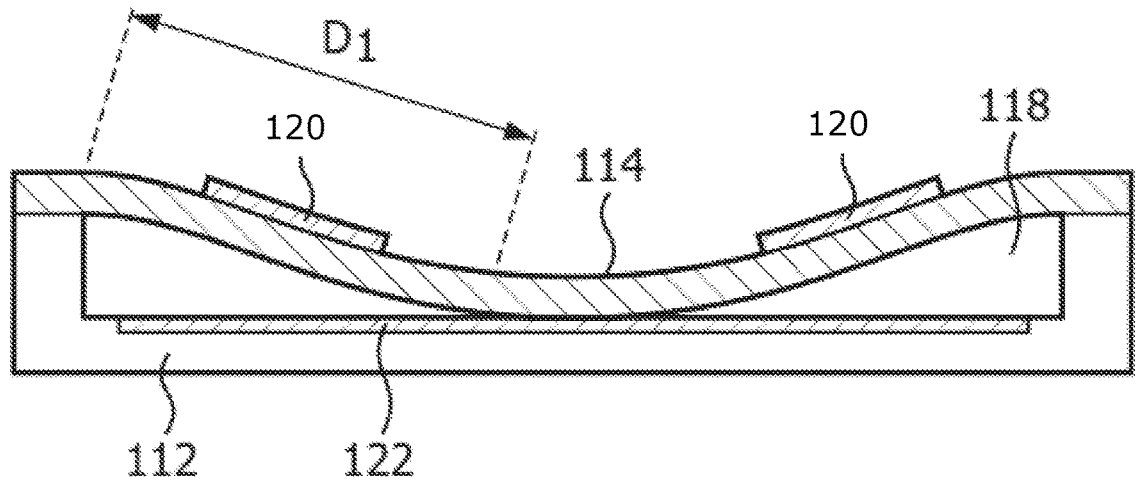
FIGS. 2a, 2b, 3a and 3b depict operating principles of such a CMUT cell.
Figure 2B:
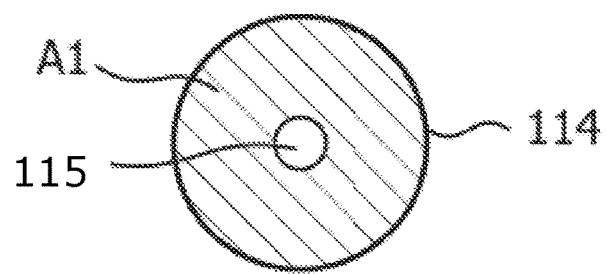
Figure 3A:
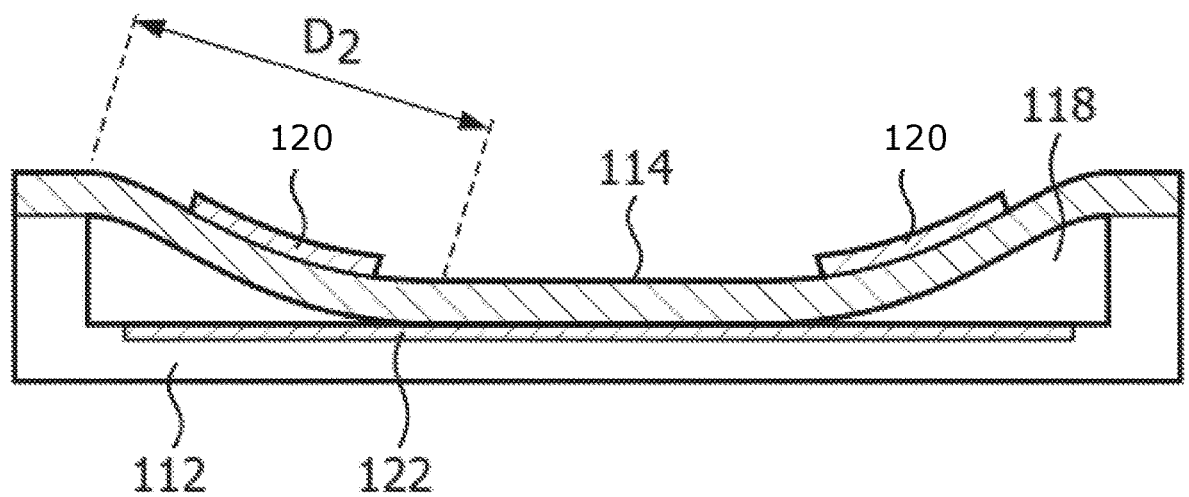

The principles behind this phenomenon are illustrated in FIGS. 2a, 2b, 3a and 3b. The cross-sectional views of FIGS. 2a and 3a illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 2a when a relatively low bias voltage is applied, whereas the distance D2 in FIG. 3a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 2a will be lower than the resonant frequency of the CMUT cell in FIG. 3a which is subject to the higher bias voltage.

Figure 3B:
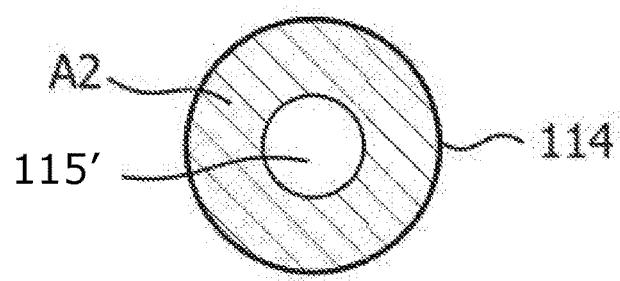

The phenomenon can also be appreciated from the two-dimensional illustrations of FIGS. 2b and 3b, which vary as a function of the effective operating area of the CMUT membrane. When the membrane 114 just touches the floor of the CMUT cell as shown in FIG. 2a, the effective vibrating area A1 of the non-contacting (free vibrating) portion of the cell membrane 114 is large as shown in FIG. 2b. The small area 115 in the center represents the center contact region of the membrane. The large area membrane will vibrate at a relatively low frequency. This area 115 is an area of the membrane 114 which is collapsed to the floor of the CMUT cell. When the membrane is pulled into deeper collapse by a higher bias voltage as in FIG. 3a, the larger central contact area 115' results in a smaller free vibrating area A2 as shown in FIG. 3b. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 4:
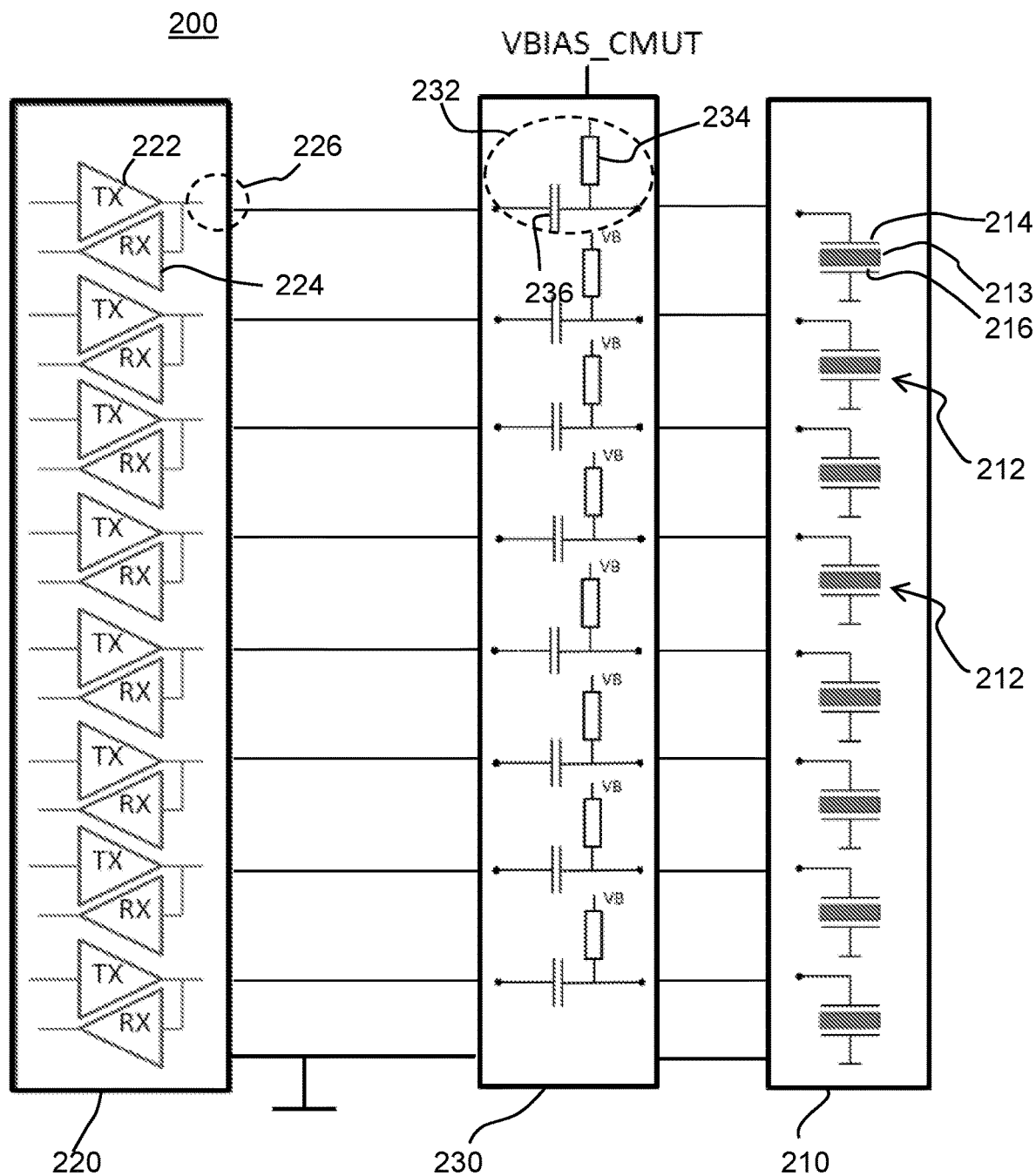
FIG. 4 shows an example of an ultrasound system having a 1D array of CMUT cells.

FIG. 4 shows a first example of an ultrasound system 200 with a drive arrangement modified in accordance with an example of the invention.

The system comprises a set 210 of ultrasound transducer devices 212, each device comprising one or more capacitive micro-machined ultrasound transducer cells 213 each having first 214 and second 216 terminals.

A drive circuit 220, in particular an ASIC, is for operating the ultrasound transducer devices. It comprises a set of transmitter circuits 222 for delivering an AC drive signal and a set of receiver circuits 224 for receiving a reflected signal, said reflected signal being representative of the reflected (by the tissue echo signals) affecting the vibration of the membrane 114. The signal transmission and reception is at a drive circuit port 226 associated with at least one of the ultrasound transducer devices.

An intermediate circuit 230 is between the drive circuit 220 and the set 210 of ultrasound devices. The intermediate circuit comprises an array of coupling circuits 232, each coupling circuit between a drive circuit port 226 and the associated at least one ultrasound transducer device 212. The coupling circuit comprises a buffer element 234 connected between a bias voltage VB (which connects to a global bias signal VBIAS_CMUT) and the first terminal 214 of the device 212.

This system uses an intermediate circuit as a connection link between the set 210 of CMUT transducer elements and the driving/sensing electronics. The buffer element 234 prevents a low-impedance short between the CMUT cell bias node (bias voltage terminal VB) and the counter electrode in the case of a CMUT cell drum short circuit. In this way, failure of an individual cell will not cause a breakdown of the whole CMUT array nor a breakdown of the driving electronics.

The buffer element 234 for example comprises a resistor. Each coupling circuit 232 also comprises a capacitor 236 in series with the first terminal 214 between the port 226 and the first terminal 214. The buffer element needs to have a high impedance and preferably linear at low and high frequencies. The buffer elements also need to be high-voltage (positive and negative) compliant.

Theoretically, it could be an option to integrate an inductor to compensate the capacitive behavior of the CMUT in order to improve power efficiency. However, the required inductance is rather high for integration. It also could be an option to include decoupling capacitors to stabilize the supply of the driver/receiver circuitry.

The capacitors mean that the intermediate circuit provides a reduction in cross talk between the CMUT cells. Such crosstalk is for example likely when a common capacitor is used for stabilization of the CMUT bias voltage. By providing a set of series capacitors 236, the single common capacitor is replaced by many, smaller, capacitors in a circuit array.

The implementation of FIG. 4 provides an array of bias-T units, which may be realized using a passive integration technology. The components are known as Integrated Passive Devices (IPDs) or Integrated Passive Components (IPCs).

Many components such as capacitors and resistors, and indeed functional blocks such as impedance matching circuits, harmonic filters, couplers and power combiners and dividers can be realized by the passive integration technology. The devices are generally fabricated using standard wafer fabrication technologies such as thin film and photolithography processing. The components can be designed as flip chip mountable or wire bondable components and the substrates for usually are thin film substrates like silicon, alumina or glass.

The technology offers an ideal trade-off for System in Package (SiP) integration for example due to the capability to grind the wafers below 100 μm thickness and the variety of packaging options (micro-bumping, wire bonding, copper pads) and delivery mode options (wafers delivery, tape & reel). A single design of the intermediate component may also be used with multiple different designs of CMUT array.

An integrated passive device thus enables a single unit to replace an array of discrete surface mount devices (SMD). An additional benefit of the passive integration technology is reduced complexity of combining the manufacturing of the intermediate circuit with the CMUT manufacturing workflow; this should enable an improved yield and reduce overall manufacturing cost.

3D passive integration in silicon is one preferred technology used to manufacture integrated passive devices, enabling high-density trench capacitors, MIM capacitors, resistors, high-Q inductors, PIN diodes or Zener diodes to be implemented in silicon. The passive devices can also be combined with active devices in the same package, although the intermediate circuit in this case may be entirely passive.

Passive integration technology is thus a highly efficient way of integrating tens or hundreds of passive components in a silicon die. The performances resulting from the technology exceed those obtained with traditional surface mount devices. The size of application boards can for example be reduced by a factor of more than 10. In addition, greater reliability and significant cost reductions can be achieved by replacing external SMD components by customized passive integration technology dies. An integrated passive device solution is also preferred as its layout can be matched with the layout of the CMUT array. In this way, the parasitic capacitance (to ground) on the nodes that connect the bias-T network to the CMUT elements can be minimized, which is important to limit signal attenuation (in transmit and receive modes).

One example of suitable technology is offered by the company Murata Integrated Passive Solutions S.A. (Trade Mark).

The connection link is placed physically close to the CMUT array to minimize parasitic capacitances. This connection link can be designed such that it is usable for many designs of 1D CMUT arrays.

In the example of FIG. 4, all CMUT elements are connected to a unique bias-T unit consisting of the coupling capacitor and high value resistor, which is connected to the common (shared) bias voltage node "VBIAS_CMUT".

Figure 5:
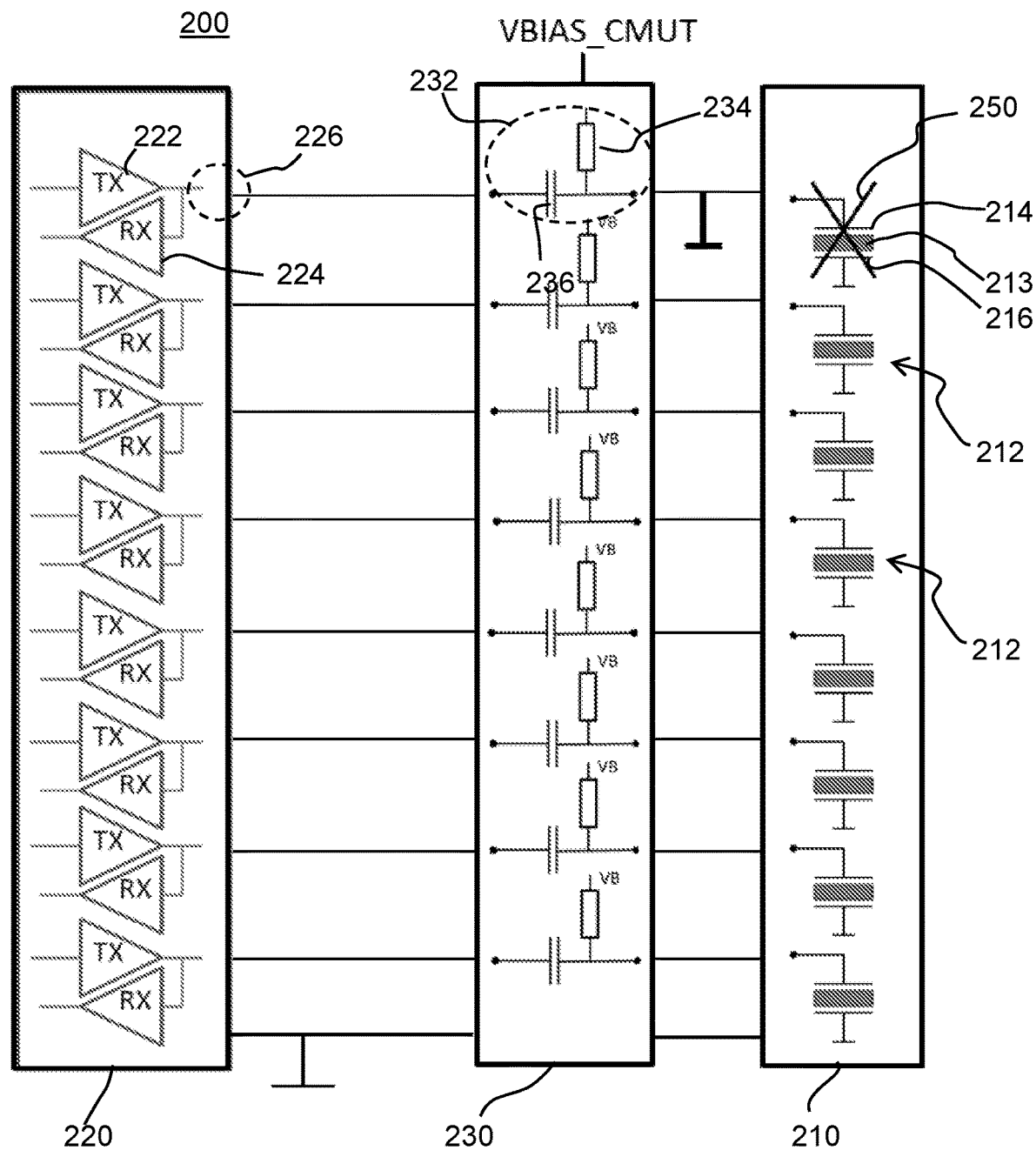
FIG. 5 shows the situation in the case of a failing (short circuit) CMUT cell.

FIG. 5 shows the situation in the case of a failing (short circuit) CMUT cell as represented by cross 250. The bias voltage across the failing CMUT cell collapses. However, due to the existence of the high value resistor 234 in series with the CMUT cell, the VBIAS_CMUT node will remain isolated, which means that the remaining CMUT cells remain operational.

By measuring the current flowing from the VBIAS_CMUT node, it is possible to detect the existence of such a failing CMUT cell. By screening all CMUT cells and measuring the acoustic response, it is possible to detect the failing element and to turn off or otherwise disable the pertaining transmit and receive circuit. This can be used to save energy.

The array of bias-T units is preferably realized in an "integrated passive devices" (IPD) technology. For example, high-density silicon capacitors may be implemented by using deep trench etching and refilling to effectively increase the vertical capacitor surface area.

The array of bias-T units may be designed such that they are usable for practically all 1D CMUT array designs.

For example, the coupling capacitors 236 may have a value of 1 nF (such as between 0.1 nF and 10 nF) and the resistors may have a value of 100 kOhm (such as 10 kOhm to 1 MOhm).

The size of a 1 nF capacitor is of the order of 0.1 mm$^2$ per capacitor for a breakdown voltage of 150 V. The size of the resistor is much smaller.

In the example shown in FIG. 4, the reference (second) terminals 216 of the CMUT cells are common to the whole CMUT array. Thus, the second terminals 216 are all connected together. The drive circuit port 226 then comprises a single drive circuit terminal. As shown in FIG. 4, the drive circuit comprises a transmitter and a receiver connected to the single drive circuit terminal 226. The output of the transmitter connects to the port and the input of the receiver connects to the port.

An alternative is to have both CMUT electrodes connected to the drive circuit 220.

Figure 6:
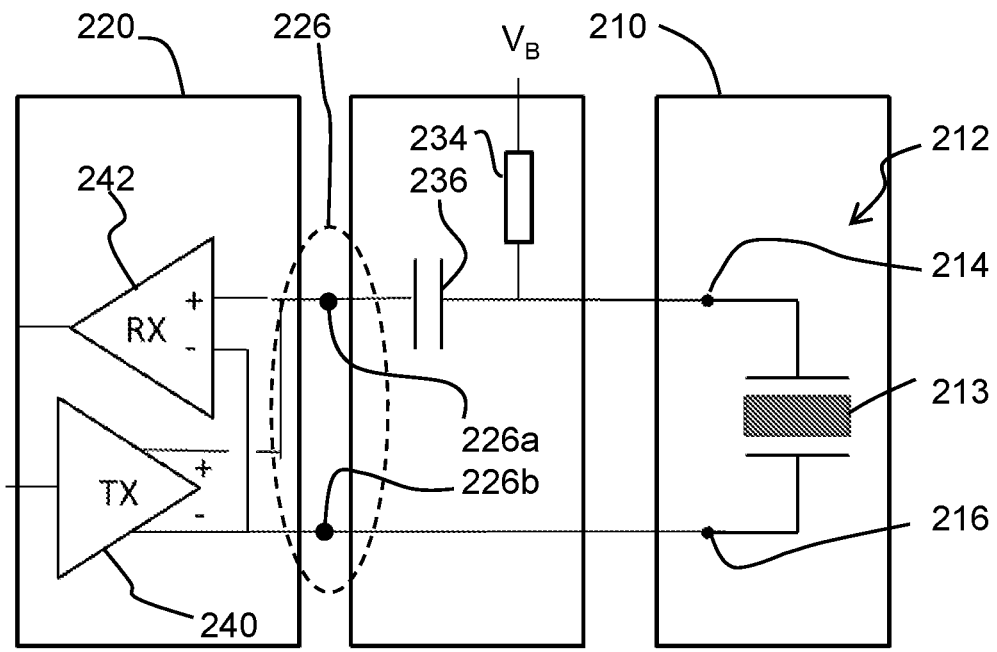
FIG. 6 shows a first example of drive arrangement with both CMUT electrodes connected to the drive circuit.

FIG. 6 shows a first example, and shows the drive circuit electronics for one transducer element. In this case, drive circuit port 226 comprises first and second drive circuit terminals 226a, 226b. This enables connection to the first and second device terminals 214, 216. The bias voltage of the CMUT cell is hidden from the drive circuit 220 by the connection link, so that control of both electrodes is easy.

In FIG. 6, the drive circuit 220 comprises a differential transmitter 240 connected to the first and second drive circuit terminals and a differential receiver 242 connected to the first and second drive circuit terminals 226a, 226b. This provides a differential implementation. The decoupling of the bias voltage achieved with the intermediate circuit enables a simpler realization of a differential implementation.

Driving a CMUT in a differential manner has the important advantage that the effective amplitude of the driving pulse can be twice the supply voltage. In practice this means that the supply voltage can be lower (e.g. 30V instead of 60V) which reduces the voltage requirements of the ASIC technology as well as the requirements on voltage regulations of the transducer system such as creepage.

Other advantages of using differential driving and receiving circuits include reduced 2nd harmonic distortion caused by electronics, better power supply rejection ratio (PSRR) due to better suppression on common mode interferers and well defined current loops (no current via the bias terminal).

Figure 7:
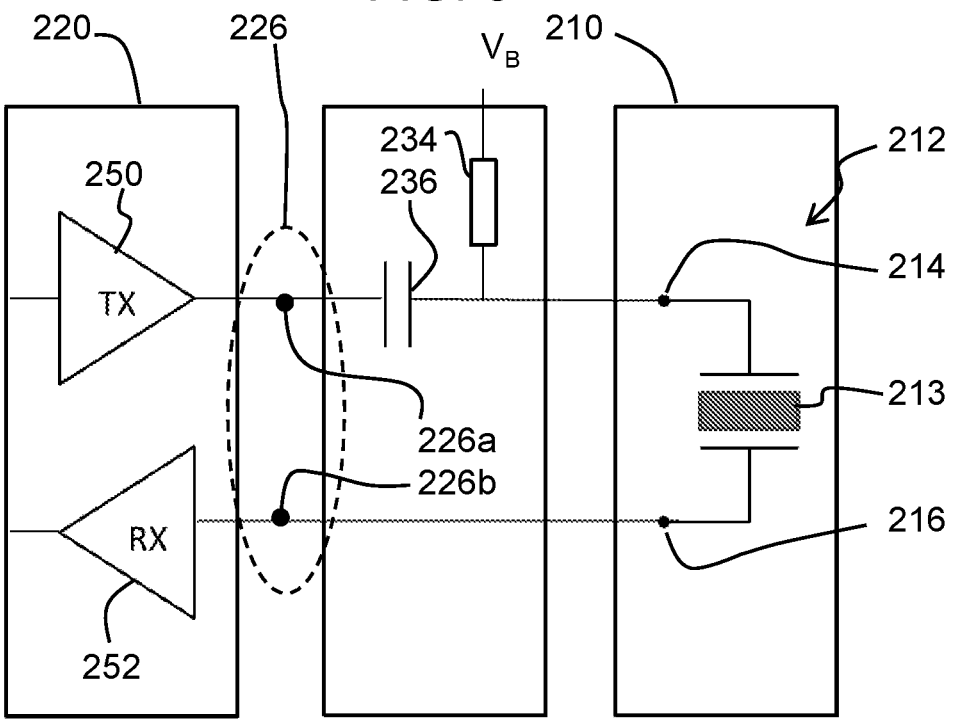
FIG. 7 shows a second example of drive arrangement with both CMUT electrodes connected to the drive circuit.

FIG. 7 shows another example which makes use of two drive circuit terminals 226a, 226b. A transmitter 250 is connected to the first drive circuit terminal 226a and a receiver 252 connected to the second drive circuit terminal 226b. This enables separated driving and receiving electronics.

In this case, the driver stimulates the first terminal of the CMUT cell while the receiver is connected to the second CMUT terminal. Due to the decoupling of the bias voltage, the transmitter and receiver ground reference can be identical which simplifies the electronics and improves the power supply rejection ratio. Furthermore, it is feasible to realize the receiver electronics using low-voltage components only which improves receiver performance. The parasitic capacitance caused by the driver will hardly influence the performance of the receiver. Finally, the well-known transmit-receive switch is not needed or can be realized in a simpler way.

In all examples above, the set of ultrasound transducer devices is shown as a 1D array of transducer devices and each drive circuit port (whether a single terminal or two terminals) connects to a single ultrasound transducer device.

However, another set of examples makes use of a 2D array of transducer devices. Thus, the set of ultrasound transducer devices is an array of rows and columns of transducer devices.

Figure 8:
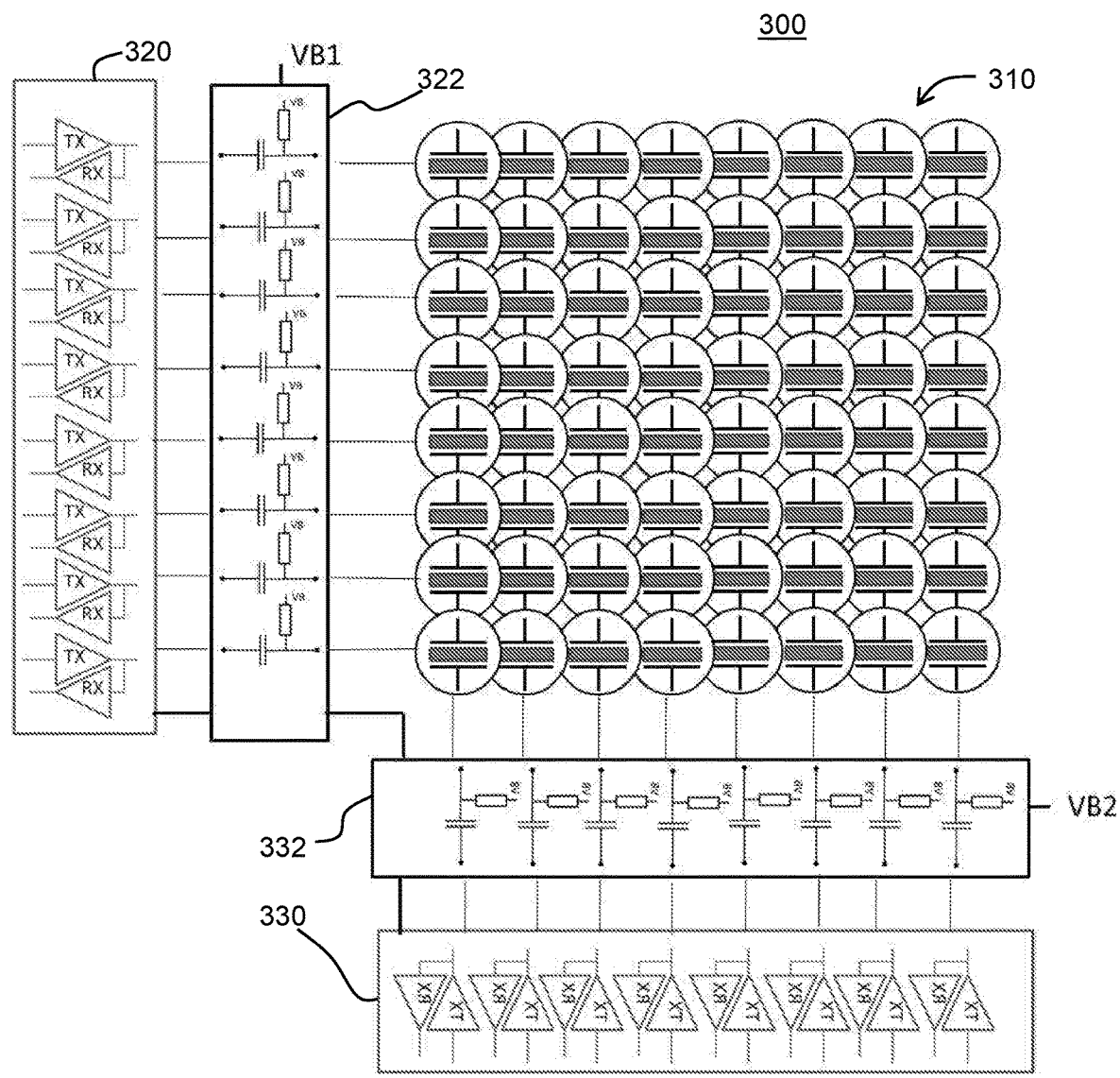
FIG. 8 shows an example of an ultrasound system having a 2D array of CMUT cells.

FIG. 8 shows an ultrasound system 300 comprising a set 310 of ultrasound transducer devices arranged as a 2D array of rows and columns.

The drive circuit described above with reference to FIG. 4 is then a first drive circuit 320 and it has an associated first intermediate circuit 322. These connect to the rows of devices.

The device further comprises a second drive circuit 330 for delivering an AC drive signal and receiving a reflected signal at a drive circuit port associated with at least one of the ultrasound transducer devices. A second intermediate circuit 332 is between the second drive circuit 330 and the set 310 of ultrasound devices. The second intermediate circuit comprises an array of coupling circuits, each coupling circuit between a second drive circuit port and the associated at least one ultrasound transducer device, and comprises a buffer element connected between a bias voltage and the second terminal.

The second drive circuit 330 and associated second intermediate circuit 332 connect to the columns of devices.

In this way, a bi-planar 1D array is formed. The rows and columns may be controlled in the same way, so that equal quality images are obtained in the two planes. Thus, FIG. 8 shows a method to drive and sense a bi-planar 1D array using two connection links. The first connection link is used to decouple the row electronics from the CMUT array, and the second link is used to decouple the column electronics from the CMUT array. The row link for example connects to the first CMUT electrode (e.g. the top electrode), and the column link connects to the second CMUT electrode (e.g. the bottom electrode).

The invention is particularly suitable for devices which comprise CMUT cells operated in collapsed mode, for which the DC bias controls the collapse. It may be used in all CMUT imaging systems, and is of particular benefit where lifetime is important and frequencies are low, for example when there are large CMUT cells.

The drive electronics for example comprises a capacitance sensing circuit which is used to measure a variation in the cell's capacitance as the response of the cell to an incident ultrasound stimulus and thereby enable ultrasound imaging. The ultrasound system for example comprises an imaging system.

Figure 9:
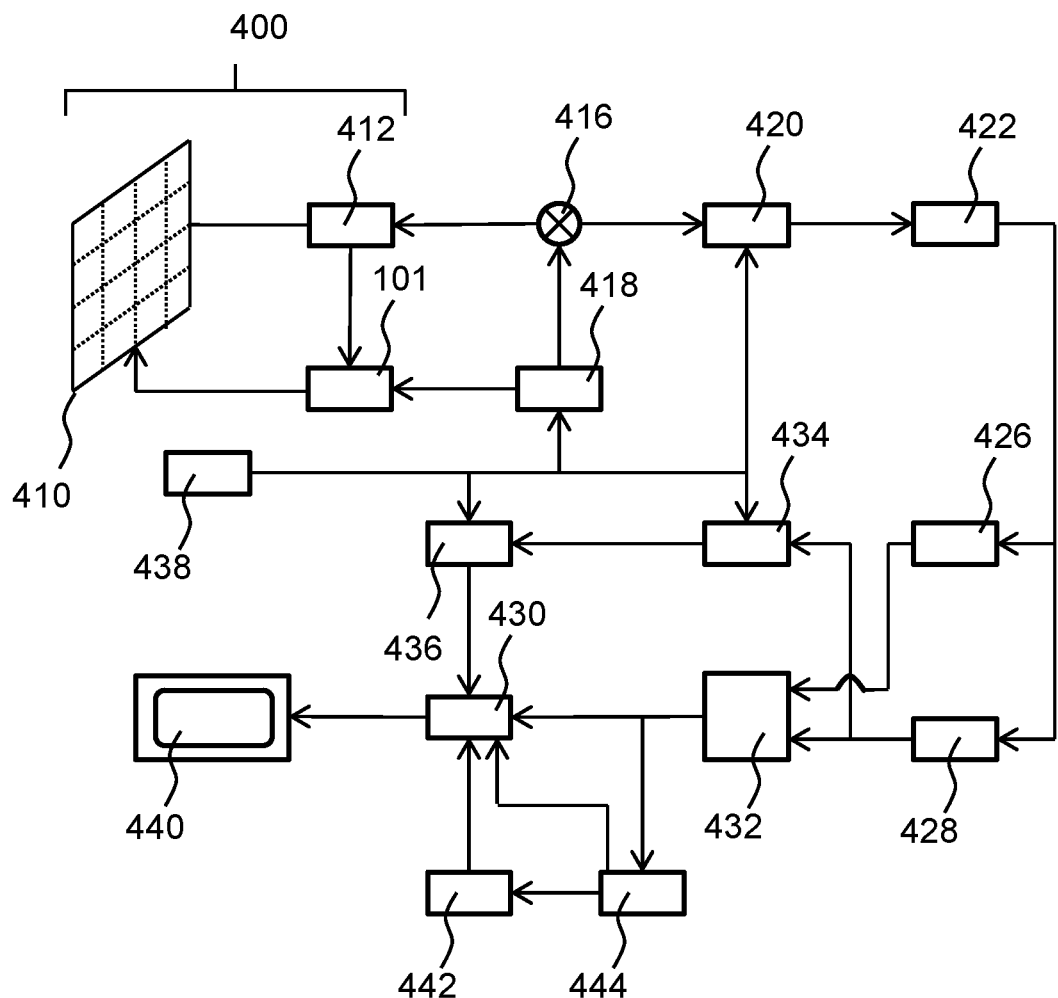
FIG. 9 schematically depicts an example embodiment of an ultrasound diagnostic imaging system which can make use of the driver arrangement of the invention.

The general operation of the CMUT system including its drive electronics can be standard and is not described in detail. However, for completeness. FIG. 9 shows an ultrasonic diagnostic imaging system with an array transducer probe 400 according to an example in block diagram form.

In FIG. 9 an ultrasound system is shown which uses CMUT cells as discussed above for transmitting ultrasonic waves and receiving echo information.

The system comprises an array transducer probe 400 which has a transducer array 410 for transmitting ultrasound waves and receiving echo information. The transducer array 410 may comprise the CMUT transducers described above. In this example, the transducer array 410 is shown as a two-dimensional array of transducers capable of scanning either a 2D plane or a three dimensional volume of a region of interest. In another example, the transducer array may be a 1D array as mentioned above.

The transducer array 410 is coupled to a microbeamformer 412 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 416 (although as discussed above, this may be omitted in some designs), which the microbeamformer 412 can be coupled to and which switches the array between transmission and reception modes, and protects the main beamformer 420 from high energy transmit signals in the case where a microbeamformer is not used and the transducer array is operated directly by the main system beamformer. The transmission of ultrasound beams from the transducer array 410 is directed by a transducer controller 418 coupled to the microbeamformer by the T/R switch 416 and a main transmission beamformer (not shown), which can receive input from the user's operation of the user interface or control panel 438. The controller 418 can include transmission circuitry arranged to drive the transducer elements of the array 410 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 418 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave or diverging imaging and focussed imaging. Different methods are distinguished by a presence of the beamforming in the transmission ("beam steered" imaging) and/or reception modes (plane wave imaging and "beam steered" imaging).

Looking first to the focusing function, the transducer array may be controlled to generate a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 418 can be coupled to control a DC bias control 445 for the transducer array. The DC bias control 445 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 412 and are then passed to a main receive beamformer 420 where the partially beamformed signals from individual patches of transducers are combined into a fully beamformed signal, referred to as radio frequency (RF) data. The beamforming performed at each stage may be carried out as described above, or may include additional functions. For example, the main beamformer 420 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 422. The signal processor 422 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 412, 420 are shown, for simplicity. In the complete system, there will also be a transmission chain with a transmission micro beamformer, and a main transmission beamformer.

The function of the micro beamformer 412 is to provide an initial combination of signals in order to decrease the number of analog signal paths. This is typically performed in the analog domain.

The final beamforming is done in the main beamformer 420 and is typically after digitization.

The transmission and reception channels use the same transducer array 410 which has a fixed frequency band. However, the bandwidth that the transmission pulses occupy can vary depending on the transmission beamforming used. The reception channel can capture the whole transducer bandwidth (which is the classic approach) or, by using band-pass processing, it can extract only the bandwidth that contains the desired information (e.g. the harmonics of the main harmonic).

The RF signals may then be coupled to a B mode (i.e. brightness mode, or 2D imaging mode) processor 426 and a Doppler processor 428. The B mode processor 426 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 428 processes temporally distinct signals arising from tissue movement and blood flow for the detection of moving substances, such as the flow of blood cells in the image field. The Doppler processor 428 typically includes a wall filter with parameters set to pass or reject echoes returned from selected types of materials in the body.

The structural and motion signals produced by the B mode and Doppler processors are coupled to a scan converter 432 and a multi-planar reformatter 444. The scan converter 432 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 440. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 442 converts the echo signals of a 3D data set into a projected 3D image as viewed from a given reference point as described in U.S. Pat. No. 6,530,885 (Entrekin et al.).

The 2D or 3D images are coupled from the scan converter 432, multi-planar reformatter 444, and volume renderer 442 to an image processor 430 for further enhancement, buffering and temporary storage for display on an image display 440. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 428 and tissue structure information produced by the B mode processor 426 are coupled to a quantification processor 434. The quantification processor produces measures of different flow conditions such as the volume rate of blood flow in addition to structural measurements such as the sizes of organs and gestational age. The quantification processor may receive input from the user control panel 438, such as the point in the anatomy of an image where a measurement is to be made.

Output data from the quantification processor is coupled to a graphics processor 436 for the reproduction of measurement graphics and values with the image on the display 440, and for audio output from the display device 440. The graphics processor 436 can also generate graphic overlays for display with the ultrasound images. These graphic overlays can contain standard identifying information such as patient name, date and time of the image, imaging parameters, and the like. For these purposes the graphics processor receives input from the user interface 438, such as patient name. The user interface is also coupled to the transmit controller 418 to control the generation of ultrasound signals from the transducer array 6 and hence the images produced by the transducer array and the ultrasound system. The transmit control function of the controller 418 is only one of the functions performed. The controller 418 also takes account of the mode of operation (given by the user) and the corresponding required transmitter configuration and bandpass configuration in the receiver analog to digital converter. The controller 418 can be a state machine with fixed states.

The user interface is also coupled to the multi-planar reformatter 444 for selection and control of the planes of multiple multi-planar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the micro-beamformer 412 and/or the Doppler processor 428 may be omitted, the ultrasound probe 410 may not have 3D imaging capabilities and so on. Other variations will be apparent to the skilled person.

The description above relates to operation in collapsed mode, but the invention can be applied equally when the cells are operated in non-collapsed mode.

The intermediate circuit may be formed as a single passive integrated technology circuit, e.g. a single flip chip or wire bond circuit. However, for larger arrays of coupling circuits, there may be multiple passive integrated technology circuits, e.g. between 2 and 5 such circuits, wherein each such circuit has 10 to 200 individual coupling circuits. Where there are first and second intermediate circuits, they are preferably separate passive integrated technology circuits, although in principle they could be integrated as a single unit.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound system, comprising:
a set of ultrasound transducer devices, each device comprising one or more capacitive micro-machined ultrasound transducer cells each having first and second terminals;
a drive circuit for operating the set of ultrasound transducer devices, the drive circuit arranged to deliver an AC drive signal and receive a reflected signal at a drive circuit port associated with at least one of the set of ultrasound transducer devices, wherein the drive circuit comprises an ASIC; and
an intermediate circuit between the drive circuit and the set of ultrasound transducer devices, wherein the intermediate circuit comprises an array of coupling circuits, each coupling circuit coupling the drive circuit port and the associated at least one of the set of ultrasound transducer devices, and comprising a buffer element connected between a bias voltage terminal (VB) and the first terminal and a capacitor in series between the first terminal and the drive circuit port, wherein the intermediate circuit comprises a passive integration technology circuit.

2. The ultrasound system as claimed in claim 1, wherein the buffer element comprises a resistor.

3. The ultrasound system as claimed in claim 1, wherein the second terminals are all connected together, and the drive circuit port comprises a single drive circuit terminal.

4. The ultrasound system as claimed in claim 3, wherein the drive circuit comprises a transmitter and a receiver connected to the single drive circuit terminal.

5. The ultrasound system as claimed in claim 1, wherein the drive circuit port comprises first and second drive circuit terminals, wherein the drive circuit comprises a differential transmitter connected to the first and second drive circuit terminals and a differential receiver connected to the first and second drive circuit terminals.

6. The ultrasound system as claimed in claim 1, wherein the drive circuit port comprises first and second drive circuit terminals, wherein the drive circuit comprises a transmitter connected to the first drive circuit terminal and a receiver connected to the second drive circuit terminals.

7. The ultrasound system as claimed in claim 1, wherein the set of ultrasound transducer devices is a 1D array of transducer devices and each drive circuit port connects to a single ultrasound transducer device.

8. The ultrasound system as claimed in claim 1, wherein the intermediate circuit is located physically proximate to the set of ultrasound transducer devices.

9. The ultrasound system as claimed in claim 1, wherein each of the set of ultrasound transducer devices comprises a capacitive micromachined ultrasonic transducer (CMUT) cell that is adapted to be operated in a collapsed mode.

10. The ultrasound system as claimed in claim 1, wherein each of the set of ultrasound transducer devices comprises a capacitive micromachined ultrasonic transducer (CMUT) cell, each CMUT cell comprising:
a substrate;
a first electrode connected to the substrate formed around a central axis of the cell;
a flexible membrane, wherein the flexible membrane is at least partially spatially separated from the first electrode; and
a second electrode connected to the flexible membrane, wherein the second electrode is concentric with the first electrode.

11. An ultrasound system, comprising:
a set of ultrasound transducer devices comprising an array of rows and columns of transducer devices, each of the set of ultrasound transducer devices comprising one or more capacitive micro-machined ultrasound transducer cells each having first and second terminals;
a first drive circuit for operating the set of ultrasound transducer devices, the first drive circuit arranged to deliver an AC drive signal and receive a reflected signal at a first drive circuit port associated with at least one of the set of ultrasound transducer devices, wherein the first drive circuit comprises an ASIC;
a first intermediate circuit between the first drive circuit and the set of ultrasound transducer devices, the first intermediate circuit comprising an array of coupling circuits, each coupling circuit coupling the first drive circuit port and the associated at least one of the set of ultrasound transducer devices, and comprising a first buffer element connected between a bias voltage terminal (VB) and the first terminal and a capacitor in series between the first terminal and the first drive circuit port, wherein the first intermediate circuit comprises a passive integration technology circuit, and each port of the first drive circuit connects to the first terminals of a row of ultrasound transducer devices through the first intermediate circuit;
a second drive circuit arranged to deliver an AC drive signal and receive a reflected signal at a second drive circuit port associated with at least one of the set of ultrasound transducer devices, wherein the second drive circuit comprises an ASIC; and
a second intermediate circuit between the second drive circuit and the set of ultrasound transducer devices, wherein the second intermediate circuit comprises an array of coupling circuits, each coupling circuit between the second drive circuit port and the associated at least one of the set of ultrasound transducer devices, and comprising a second buffer element connected between a bias voltage terminal and the second terminal and a capacitor in series between the second terminal and the second drive circuit port, wherein each port of the second drive circuit connects to the second terminals of a column of ultrasound transducer devices through the second intermediate circuit, wherein the second intermediate circuit comprises a passive integration technology circuit.

12. The ultrasound system as claimed in claim 11, wherein the second buffer element of each coupling circuit of the second intermediate circuit also comprises a resistor.

13. The ultrasound system as claimed in claim 11, wherein each of the first and second buffer elements comprise a resistor.

14. The ultrasound system as claimed in claim 11, wherein the second terminals are all connected together, and the first and second drive circuit ports each comprise a single drive circuit terminal.

15. The ultrasound system as claimed in claim 14, wherein the first drive circuit comprises a transmitter and a receiver connected to the single drive circuit terminal.

16. The ultrasound system as claimed in claim 11, wherein the first drive circuit port comprises first and second drive circuit terminals, wherein the first drive circuit comprises a differential transmitter connected to the first and second drive circuit terminals and a differential receiver connected to the first and second drive circuit terminals.

17. The ultrasound system as claimed in claim 11, wherein the first drive circuit port comprises first and second drive circuit terminals, wherein the first drive circuit comprises a transmitter connected to the first drive circuit terminal and a receiver connected to the second drive circuit terminals.

18. The ultrasound system as claimed in claim 11, wherein the set of ultrasound transducer devices is a 1D array of transducer devices and each drive circuit port connects to a single ultrasound transducer device.

19. The ultrasound system as claimed in claim 11, wherein the first and second intermediate circuits are located physically proximate to the set of ultrasound transducer devices.

20. The ultrasound system as claimed in claim 11, wherein each of the set of ultrasound transducer devices comprises a capacitive micromachined ultrasonic transducer (CMUT) that is adapted to be operated in a collapsed mode.

21. The ultrasound system as claimed in claim 11, wherein each of the set of ultrasound transducer devices comprises a capacitive micromachined ultrasonic transducer (CMUT) cell, each CMUT cell comprising:
   a substrate;
   a first electrode connected to the substrate formed around a central axis of the cell;
   a flexible membrane, wherein the flexible membrane is at least partially spatially separated from the first electrode; and
   a second electrode connected to the flexible membrane, wherein the second electrode is concentric with the first electrode.

* * * * *